(12) United States Patent
Chung et al.

(10) Patent No.: US 6,610,313 B2
(45) Date of Patent: Aug. 26, 2003

(54) LYSOPHOSPHOLIPIDS COMPOSITION WITH WATER SOLUBILITY

(75) Inventors: GukHoon Chung, Kyonggi-do (KR); Young-Lae Yang, Kyonggi-do (KR); Ui C Koh, Seoul (KR)

(73) Assignee: Doosan Corporation, Seoul (KR)

( * ) Notice: Subject to any disclaimer, the term of this patent is extended or adjusted under 35 U.S.C. 154(b) by 46 days.

(21) Appl. No.: 10/004,927

(22) Filed: Dec. 7, 2001

(65) Prior Publication Data

US 2003/0059395 A1 Mar. 27, 2003

(30) Foreign Application Priority Data

Sep. 27, 2001 (KR) .......................................... 2001-60015

(51) Int. Cl.[7] .................................................. A61K 7/00
(52) U.S. Cl. ....................................................... 424/401
(58) Field of Search .......................................... 424/401

(56) References Cited

U.S. PATENT DOCUMENTS

| 5,126,155 A | * | 6/1992 | Palta et al. | 426/331 |
| 5,153,125 A | * | 10/1992 | Kobayashi | 435/128 |
| 6,509,055 B1 | * | 1/2003 | Garnett | 426/662 |

* cited by examiner

*Primary Examiner*—Theodore J. Criares
*Assistant Examiner*—Jennifer Kim
(74) *Attorney, Agent, or Firm*—Browdy and Neimark, P.L.L.C.

(57) ABSTRACT

The present invention discloses improved lysophospholipids composition having water-solubility in order to solve a conventional problem accompanying only the use of LPE as an anti-aging lysophospholipid caused by water-insoluble property thereof, comprising subsidiary lysophospholipid components, that is, LPI and LPC other than LPE to inhibit aging processional lysophospholipids, thereby forming an enhanced water-soluble lysophospholipids composition conveniently useable in plants and/or animals applications.

7 Claims, 3 Drawing Sheets

LYSOPHOSPHOLIPIDS COMPOSITION WITH WATER SOLUBILITY

BACKGROUND OF THE INVENTION

1. Field of the Invention

The present invention relates to lysophospholipids with water solubility, and more particularly, to desired lysophospholipids composition with water solubility including lysophosphatidylethanolamine (hereinafter referred to as "LPE"), lysophosphatidylinositol (hereinafter referred to as "LPI") and lysophosphatidylcholine (hereinafter referred to as "LPC").

Other than said LPE, LPI and LPC, known are different kinds of lysophospholipids such as lysophosphatidylglycerol (LPG), lysophosphatidylserine (LPS) and/or lysophosphatidylic acid (LPA). However, the present invention is directed to provide a lysophospholipids composition having excellent water-solubility enabling to easily apply it to various applications simultaneously with improved anti-aging effects of plants including fruits and animals by comprising desired contents of LPE, LPI and LPC in the composition.

2. Description of the Related Art

Conventionally, LPE among the lysophospholipids composition is known to substantially serve for the ripening and/or aging of fruits. For instance, U.S. Pat. Nos. 5,220,341 and 5,126,155 disclose that LPE inhibits the aging of leaves and fruits of tomato and also extends the storage time of tomato after harvesting.

The aging inhibition effect of LPE is usually accomplished by controlling the reaction of phospholipase D which is well known as an important enzyme to intermediate the degeneration of membrane phospholipids at the initial step of the aging process of plants. It is also known that said functional effect of LPE to phospholipase D varies depending on amounts used thereof, and usually increases in proportion to length of acyl chains contained in LPE and/or amount of unsaturated parts.

As described above, the inhibition effect of phospholipase D by lysophospholipids, resulting in the anti-aging inhibition effect is most excellent for LPE, though it gradually decreases for LPI and LPC in series so that LPC shows only a slight activity to inhibit the phospholipase D. Whereas it is found that LPG, LPS and LPA affect opposite to the effects of said LPE, LPI and LPC and the extent of the opposite effect is enlarged in their order. For example, LPA cannot inhibit the generation of phospholipase D, rather, it accelerates said generation to lead no activity to inhibit the aging of plants. (See Proc. Natl. Acad. Sci. USA, Vol.94, pp12717–12721, November 1997 Plant Biology which is incorporated for reference).

According to a result of studying as described above, in order to obtain anti-aging property, only LPE will be preferably used. However, since it is difficult to obtain LPE by isolation and purification thereof, in addition to, LPE itself is not water-soluble, it still has a problem not to preferably apply to plants and animals.

SUMMARY OF THE INVENTION

It is, therefore, an object of the present invention to provide a lysophospholipids composition with water solubility comprising LPI and LPC in addition to LPE, wherein the LPI and LPC have subsidiary effects for the inhibition of aging, and the overall composition is water-soluble, thereby the composition is capable of removing the above described drawback induced by the water-insoluble property of LPE when it is only employed as lysophospholipid having excellent efficiency to inhibit aging process so that the lysophospholipids composition can be efficiently and easily applied to plants and animals.

To achieve the above object, there is provided a water-soluble composition, particularly, a lysophospholipids composition with water solubility including LPE and LPC, in which the content of LPC is ranged of 20 to 60% by weight if the content of LPE is 0.1 to 5% by weight based on total weight of water.

Furthermore, there is preferably provided another lysophospholipids composition with water solubility comprising LPE, LPC and LPI, in which LPC, LPI and LPE are contained in the amounts of 10–50, 10–50 and 40–60% by weight, respectively, if the content of LPE is over 0.5% by weight and less than 2% by weight based on the weight of water.

There is also provided alternative lysophospholipids composition with water solubility comprising LPE, LPC and LPI, in which LPC, LPI and LPE are contained in the amounts of 10–70, 10–70 and more than 20% by weight, respectively, if the content of LPE is over 0.1% by weight and less than 1% by weight based on the weight of water.

Finally, there is further provided a lysophospholipids composition with water solubility comprising LPE, LPC and LPI, in which LPC and LPI are contained in the amounts of 10–90% and 10–90% by weight, respectively, if the content of LPE is less than 0.1% by weight based on the weight of water.

The respective lysophospholipid components forming the lysophospholipids composition with water solubility according to the present invention may include natural materials, processed one from the natural materials by means of isolation and purification processes and/or artificially synthesized one.

Said natural material itself and/or separated and purified one from the natural material include, for example, soybean phospholipids and yolk phospholipids.

BRIEF DESCRIPTION OF THE DRAWINGS

The above objects, features and advantages of the present invention will become more apparent from the following detailed description when taken in conjunction with the accompanying drawings, in which.

DETAILED DESCRIPTION OF THE PREFERRED EMBODIMENT

Figure 1:
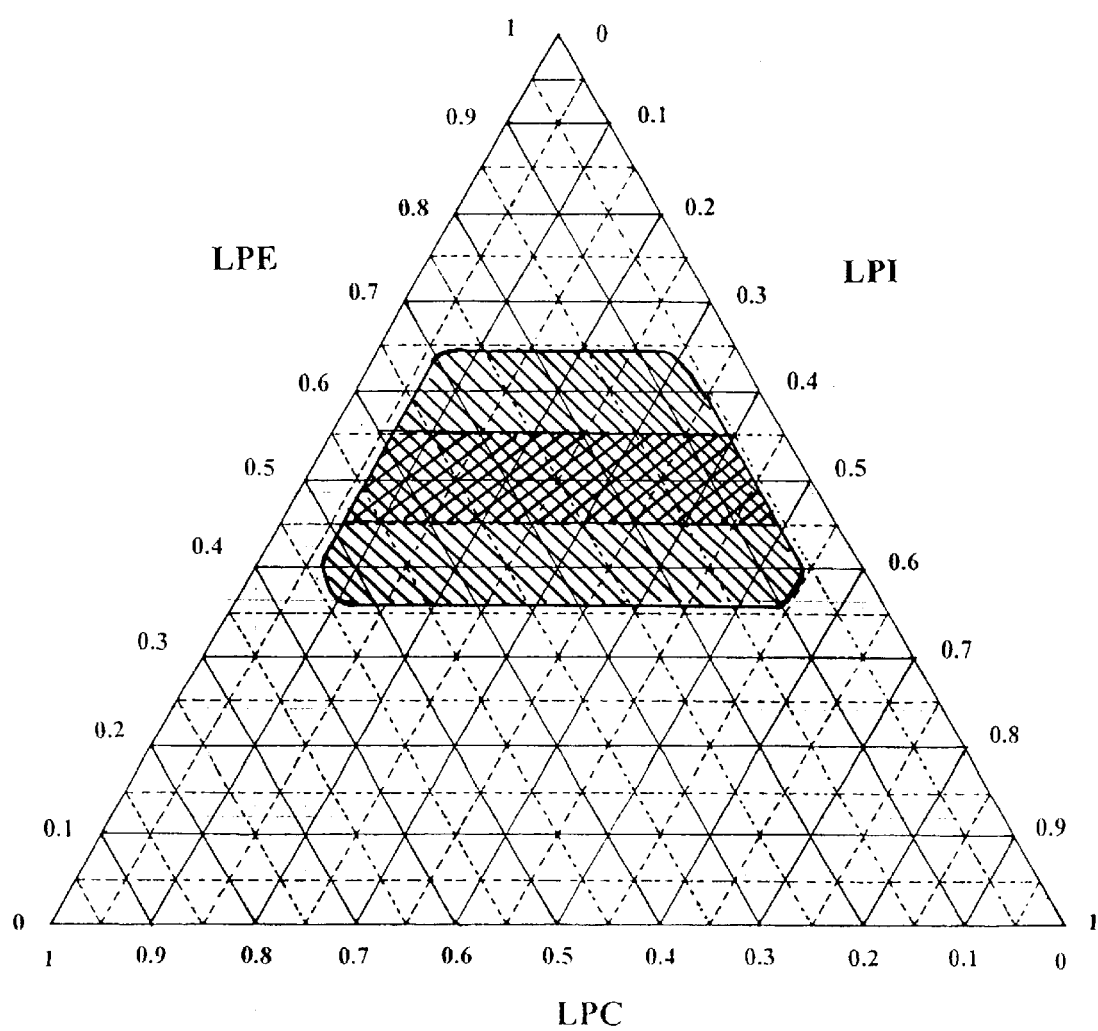
FIG. 1 illustrates a solubility graph along to the relative ratios of components such as LPE, LPC and LPI among overall lysophospholipids when the content of LPE is 1% by weight based on total weight of water.

A preferred embodiment of the present invention will now be described with reference to the accompanying drawings.

The present invention is explained in detail by reference to the following examples. Said examples were practically embodied with soybean-yolk phospholipids, however, the present invention is not intended to be limited thereby. Hereinafter, "%" represents "% by weight" based on 100% by weight of total composition.

In the following description, same drawing reference numerals are used for the same elements even in different drawings.

EXAMPLE 1
<Combination of Two Kinds of Lysophospholipids>

Combination of LPC:LPI (LPC:LPI) combination is always water-soluble, that is, has good water solubility under the content level of less than 50% for overall lysophospholipids based on total amount of water.

Combination of LPE:LPC

After fixing contents of LPE in water into 5%, 2.5%, 1%, 0.5% and 0.1%, the respective LPE solutions obtained above are combined with different amounts of LPC ranged from 10 to 90% to form desired LPE:LPC combinations. Thereafter, the combinations begin to dissolve in water by heating them in a water bath at 60° C. By decreasing the temperature to ambient temperature, it is found that the solution has about 20–60% of LPC content and forms an opaque suspension and is a little deposited out of the water due to high concentration of total lysophospholipid.

Combination of LPE:LPI

After fixing contents of LPE in water into 5%, 2.5%, 1%, 0.5% and 0.1%, the respective LPE solutions obtained above are combined with different amounts of LPI ranged from 10 to 90% to form desired LPE:LPI combinations. Thereafter, the combinations begin to dissolve in water by heating them in a water bath at 60° C. By decreasing the temperature to ambient temperature, it is found that the phospholipid part is not dissolved but deposited out of the water independent of LPI content.

From the result shown in Example 1, it is understood that LPC plays an important role to the solubility of lysophospholipids composition in water. Thus, it is confirmed that by controlling the content of LPC in the lysophospholipids composition it can have desired degree of water-solubility.

On the other hand, in view of the anti-aging property, LPE is most excellent whereas it decreases somewhat for LPI and LPC in order. Therefore, it will be expected that the lysophospholipid product requires a particular composition of respective components to have desired water-solubility in order to accomplish the superior aging inhibition activity and put it into practice in the plant and animal applications. In order to achieve the purpose of the present invention, the lysophospholipids composition necessarily includes LPE.

Accordingly, as shown in Example 2 below, the water-solubility of lysophospholipids composition according to the present invention was examined along the composition ratios of LPI and LPC under the condition of fixed content of LPE based on total weight of water.

EXAMPLE 2
<Combination of Three Kinds of Lysophospholipids>

–2% or more of LPE to water content

When the content of LPE is more than 2% by weight based on total amount of water, the combined material become to water-soluble under heating in a water bath at 60° C. for all of the composition ratios of LPI and LPC. However, the phospholipid part is deposited out of water by decreasing the temperature to ambient temperature. It is presumed that this result is due to excess amount of lysophospholipids over the level of water-solubility being included in the combination.

–1% LPE to water content

When the content of LPE is fixed to 1% by weight based on total weight of water, the combined materials containing LPC(10–50%), LPI(10–50%) and LPE(40–60%) among overall lysophospholipids become water-soluble state under heating in a water bath at 60° C. The phospholipid part is under the water-soluble state even at the ambient temperature. Particularly, the lysophospholipid parts at the ratios of LPE:LPC:LPI such as (50:10:40), (50:20:30), (50:30:20) and (50:40:10) are completely dissolved and form transparent solutions.

However, in case of 70% or more of LPE, the lysophospholipid part is deposited with water-insoluble result. On the contrary, for less than 30% of LPE, total amount of overall lysophospholipids is increased and saturated in water due to the content of LPE being fixed to 1% based on water, thereby exhibiting no further dissolution of the lysophospholipids.

FIG. 1 shows a solubility graph along to the relative ratios of components such as LPE, LPC and LPI among overall lysophospholipids when the content of LPE is 1% by weight based on total weight of water. Oblique lined area represents the composition ratios of LPE:LPC:LPI in which the lysophospholipid part is dissolved in water, especially, the double-oblique lined area shows the ratios in which the lysophospholipid part forms a transparent solution. This result is substantially same to the case that the content of LPE is over 0.5% by weight and less than 2% by weight based on water. (See FIG. 1, supra.)

–0.5% LPE to water content

When the content of LPE is fixed to 0.5% by weight based on total weight of water, the combined materials containing LPC(10–70%), LPI(10–70%) and LPE(20% or above) among overall lysophospholipids become water-soluble state under heating in a water bath at 60° C. The phospholipids are under the water-soluble state even at the ambient temperature. Particularly, the lysophospholipid parts at the ratios of LPE:LPC:LPI such as (60:10:30), (70:10:20), (70:20:10) and (80:10:10) (oblique lined area in FIG. 2) are partially dissolved and form opaque solutions. Whereas the lysophospholipids at the other composition ratios excluding said ratios (double-oblique lined area in FIG. 2) are completely water-soluble and form transparent solutions.

However, in case of less than 10% LPE, the lysophospholipids are water-insoluble because amount of overall lysophospholipids is increased and saturated in water due to the content of LPE being fixed to 0.5% based on water.

Figure 2:
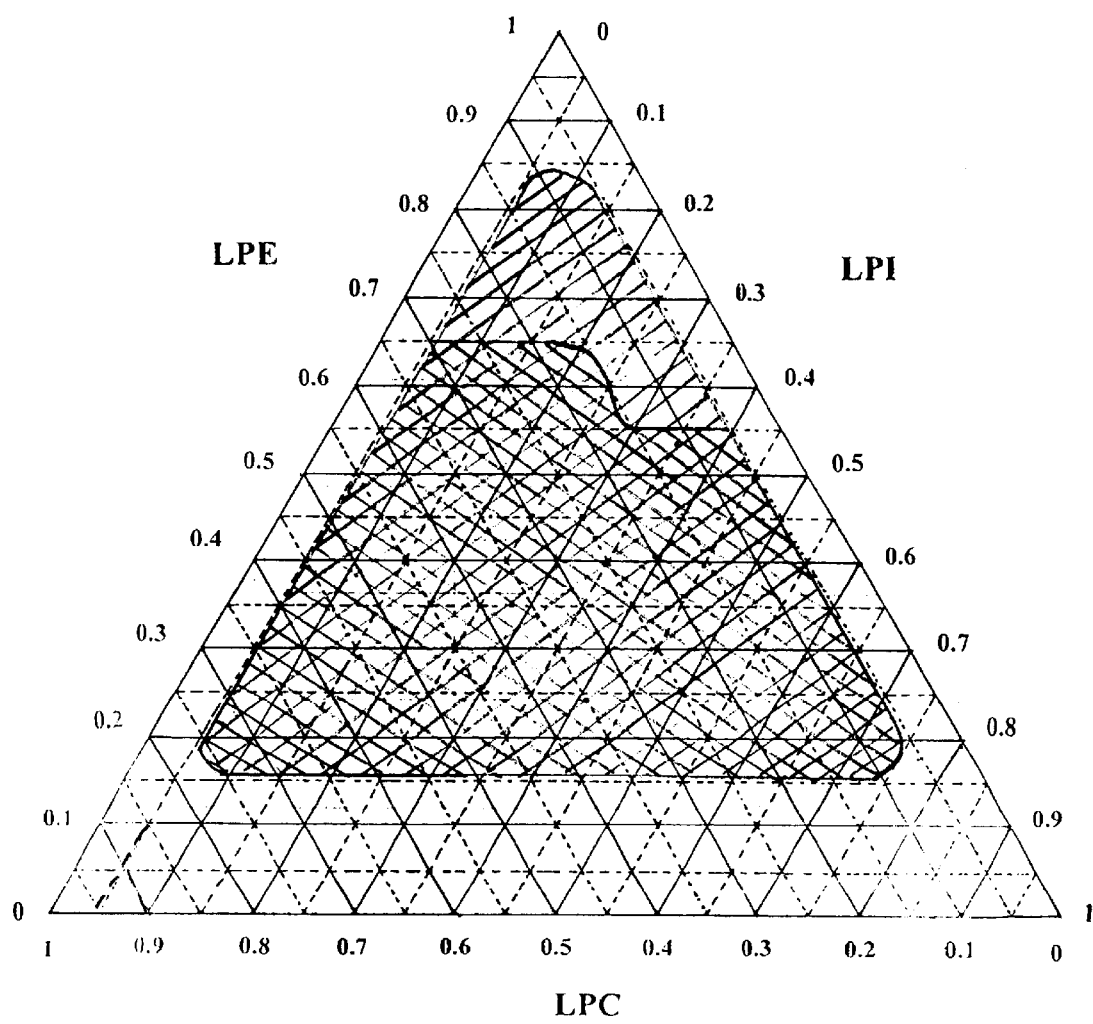
FIG. 2 illustrates another solubility graph along to the relative ratios of components such as LPE, LPC and LPI among overall lysophospholipids when the content of LPE is 0.5% by weight based on total weight of water.

FIG. 2 shows another solubility graph along to the relative ratios of components such as LPE, LPC and LPI among overall lysophospholipids when the content of LPE is 0.5% by weight based on total weight of water. Oblique lined area represents the composition ratios of LPE:LPC:LPI in which the lysophospholipid part is dissolved in water, especially, the double-oblique lined area shows the ratios in which the lysophospholipids form a transparent solution. The solubility for over 0.1% and less than 1% LPE is substantially same to over 0.5% LPE. (See FIG. 2, supra.)

–0.1% LPE to water content

When the content of LPE is fixed to 0.1% by weight based on total weight of water and the relative ratios of LPI and LPC varies, the combined materials containing LPC (10–90%) and LPI(10–90%) among overall lysophospholipids become water-soluble state under heating in a water bath at 60° C. All of the phospholipids are under the water-soluble state and form transparent solutions even at the ambient temperature.

Figure 3:
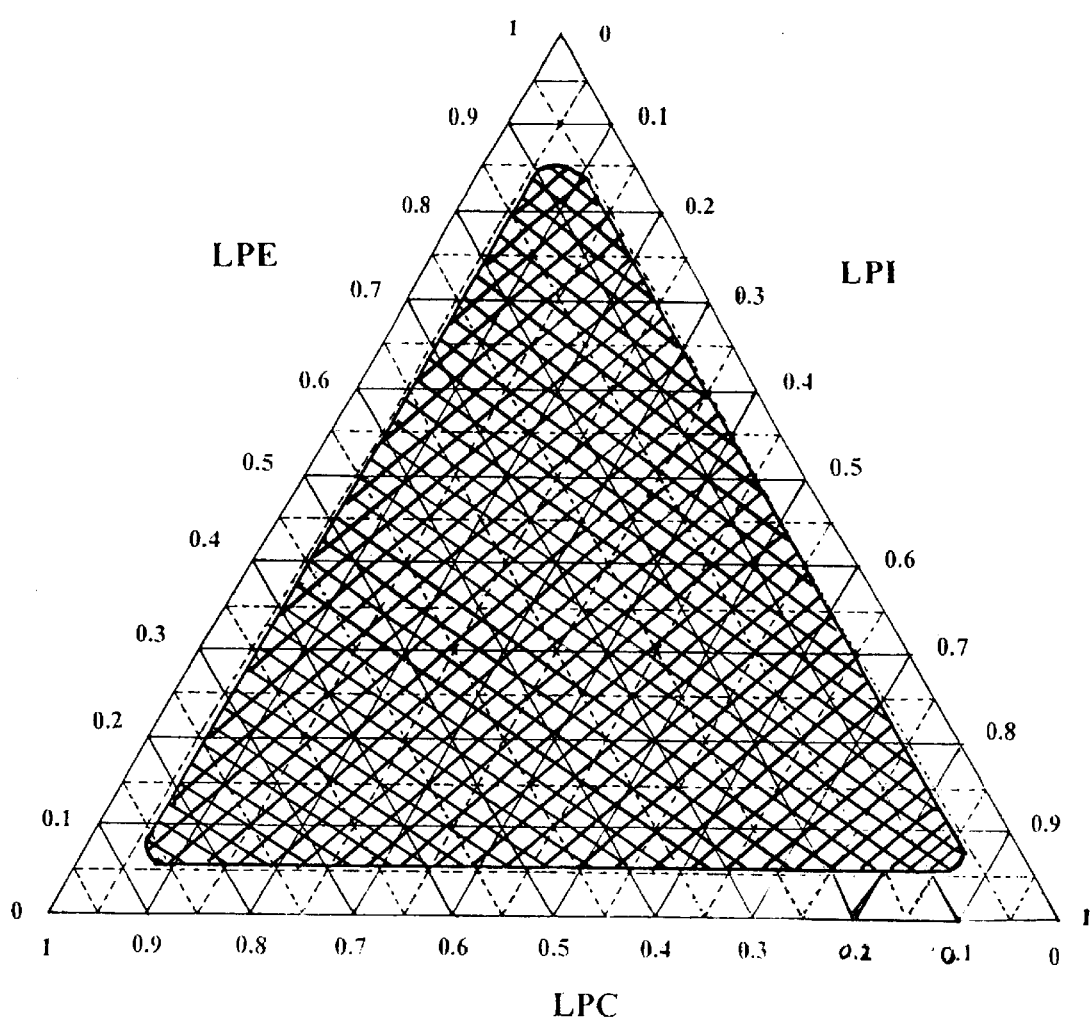
FIG. 3 illustrates further another solubility graph along to the relative ratios of components such as LPE, LPC and LPI among overall lysophospholipids when the content of LPE is 0.1% by weight based on total weight of water.

FIG. 3 further shows another solubility graph along to the relative ratios of components such as LPE, LPC and LPI among overall lysophospholipids when the content of LPE is 0.1% by weight based on total weight of water. Oblique lined area represents the composition ratios of LPE:LPC:LPI in which the lysophospholipid part is dissolved in water, especially, including the area to show the ratios in which the lysophospholipids form transparent solutions. The solubility for less than 0.1% LPE is substantially same to of 0.1% LPE. (See FIG. 3, supra.)

As described above, the lysophospholipids composition having water-solubility of the present invention comprises LPE as an excellent lysophospholipid to inhibit aging process and, in addition to, LPE and/or LPC as subsidiary lysophospholipids to inhibit aging process, thereby forming an enhanced water-soluble lysophospholipids composition conveniently useable in plants and/or animals applications.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A lysophospholipids composition having water-solubility comprising LPE and LPC, wherein the content of LPC is about 20 to 60% by weight when the content of LPE is ranged of 0.1 to 5% by weight based on amount of water.

2. A lysophospholipids composition having water-solubility comprising LPE, LPC and LPI, wherein said composition has LPC, LPI and LPE in the contents of 10 to 50%, 10 to 50% and 40 to 60% by weight, respectively, when the content of LPE is ranged over 0.5% and less than 2% by weight based on amount of water.

3. The lysophospholipids composition according to claim 2, wherein the composition ratio of (LPE:LPC:LPI) contained in said composition is any one selected from a group consisting of (50:10:40), (50:20:30), (50:30:20) and (50:40:10).

4. A lysophospholipids composition having water-solubility comprising LPE, LPC and LPI, wherein said composition has LPC, LPI and LPE in the contents of 10 to 70%, 10 to 70% and more than 20% by weight, respectively, when the content of LPE is ranged over 0.1% and less than 1% by weight based on amount of water.

5. A lysophospholipids composition having water-solubility comprising LPE, LPC and LPI, wherein the contents of LPC and LPI contained in said composition are 10 to 90% and 10 to 90%, respectively, when the content of LPE is less than 0.1% by weight based on amount of water.

6. The lysophospholipids composition according to any one of claims 1 to 5, wherein the respective lysophospholipid components forming said composition include natural materials, isolated and purified materials from the natural materials and/or artificially synthesized materials.

7. The lysophospholipids composition according to claim 6, wherein said natural materials themselves and/or isolated and purified materials from the natural materials include soybean phospholipids and yolk phospholipids.

* * * * *